United States Patent
Fukuda et al.

(10) Patent No.: US 10,102,624 B2
(45) Date of Patent: Oct. 16, 2018

(54) RADIATION IMAGE PROCESSING APPARATUS, RADIATION IMAGE PROCESSING METHOD, AND RECORDING MEDIUM HAVING RADIATION IMAGE PROCESSING PROGRAM STORED THEREIN

(71) Applicant: FUJIFILM Corporation, Tokyo (JP)

(72) Inventors: Wataru Fukuda, Ashigarakami-gun (JP); Junya Morita, Ashigarakami-gun (JP)

(73) Assignee: FUJIFILM Corporation, Minato-ku, Tokyo (JP)

( * ) Notice: Subject to any disclaimer, the term of this patent is extended or adjusted under 35 U.S.C. 154(b) by 0 days.

(21) Appl. No.: 15/431,076

(22) Filed: Feb. 13, 2017

(65) Prior Publication Data

US 2017/0236276 A1 Aug. 17, 2017

(30) Foreign Application Priority Data

Feb. 16, 2016 (JP) .................................. 2016-026615

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/025* (2013.01); *A61B 6/502* (2013.01); *A61B 6/5252* (2013.01);
(Continued)

(58) Field of Classification Search
CPC ......... A61B 6/481; A61B 6/025; A61B 6/482; A61B 6/502; A61B 6/4035
(Continued)

(56) References Cited

U.S. PATENT DOCUMENTS

| 7,269,246 B2 * | 9/2007 | Ohishi .................. A61B 6/481 378/196 |
| 2007/0053491 A1 * | 3/2007 | Schildkraut .......... A61N 5/1049 378/65 |

(Continued)

FOREIGN PATENT DOCUMENTS

| JP | 2012-166026 A | 9/2012 |
| JP | 2014-507250 A | 3/2014 |

*Primary Examiner* — Charlotte M Baker
(74) *Attorney, Agent, or Firm* — Sughrue Mion, PLLC

(57) ABSTRACT

First and second image obtaining units respectively obtain a plurality of first projection images and a plurality of second projection images by tomosynthesis imaging operations according to first and second imaging conditions. A reconstructing unit reconstructs the plurality of first and second projection images employing processes of a reconstruction process that includes a filtering process other than the filtering process, to generate a plurality of first tomographic images and a plurality of second tomographic images for each of a plurality of cross sectional planes within a subject. A subtraction processing unit generates tomographic subtraction images from the first and second tomographic images. A filtering processing unit administers filtering processes on the tomographic subtraction images, to generate processed tomographic subtraction images.

13 Claims, 8 Drawing Sheets

(51) Int. Cl.
*A61B 6/02* (2006.01)
*G06T 11/00* (2006.01)
*G06T 5/50* (2006.01)
*A61B 6/00* (2006.01)

(52) U.S. Cl.
CPC .............. *G06T 5/50* (2013.01); *G06T 11/003* (2013.01); *A61B 6/463* (2013.01); *A61B 6/481* (2013.01); *G06T 2207/10081* (2013.01); *G06T 2207/20224* (2013.01)

(58) Field of Classification Search
USPC .................. 382/131; 378/65, 5, 98.12, 196; 600/427, 431
See application file for complete search history.

(56) References Cited

U.S. PATENT DOCUMENTS

| | | |
|---|---|---|
| 2012/0238870 A1 | 9/2012 | Smith et al. |
| 2013/0044861 A1 | 2/2013 | Muller et al. |
| 2014/0072096 A1* | 3/2014 | Hoernig ................. A61B 6/025 378/5 |
| 2015/0110239 A1 | 4/2015 | Muller et al. |
| 2015/0327826 A1 | 11/2015 | Smith et al. |
| 2016/0220207 A1* | 8/2016 | Jouhikainen ........... A61B 6/482 |

* cited by examiner

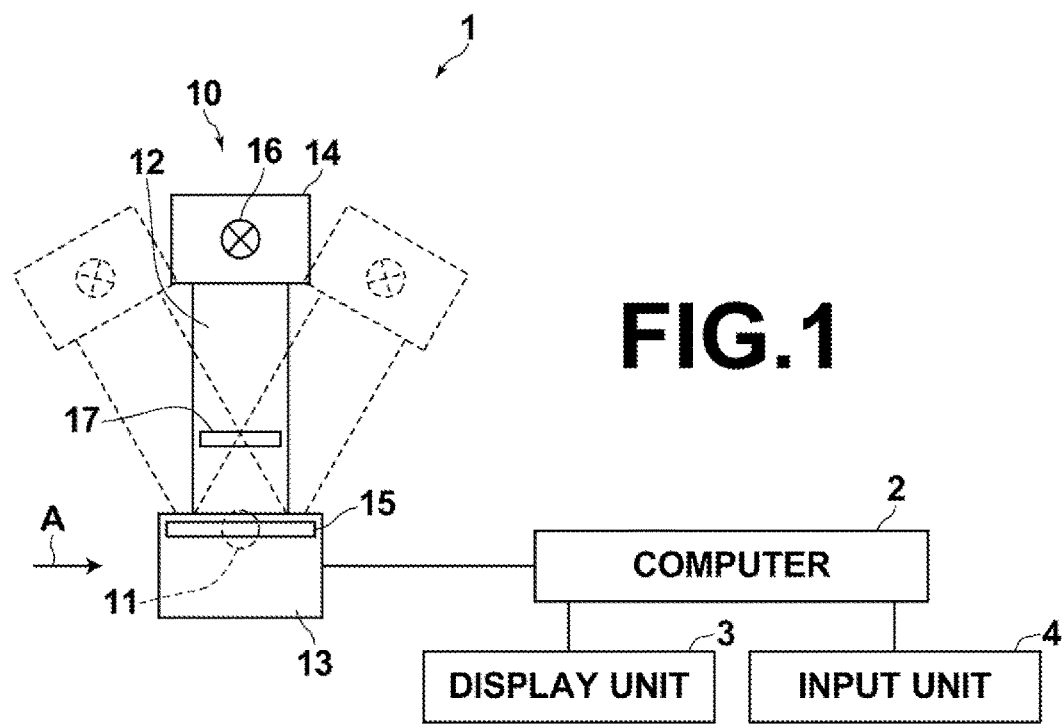
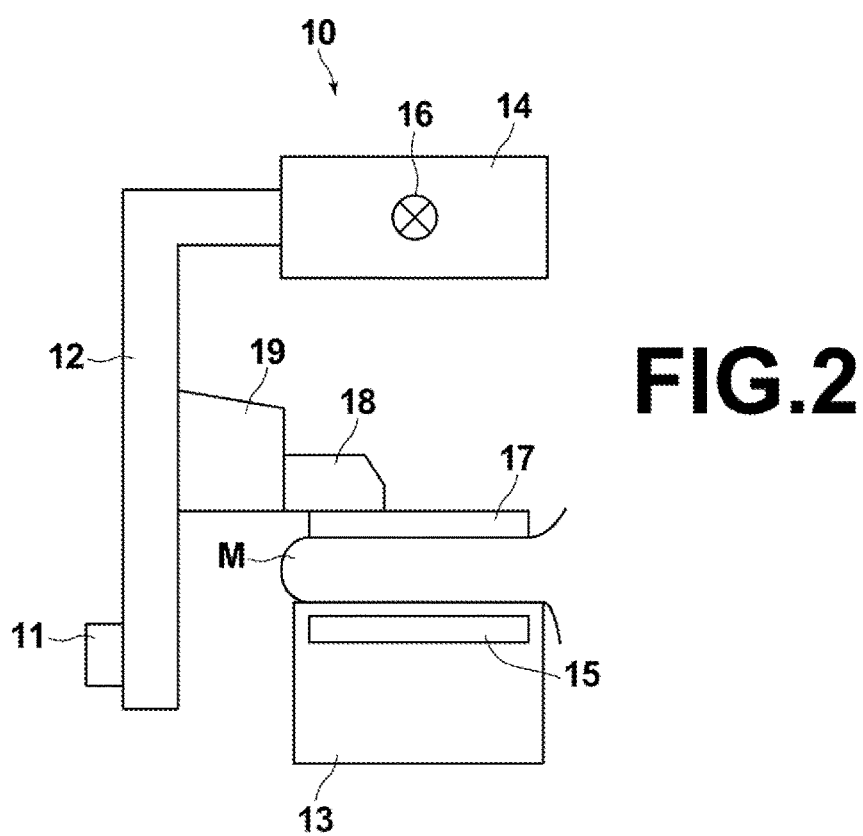

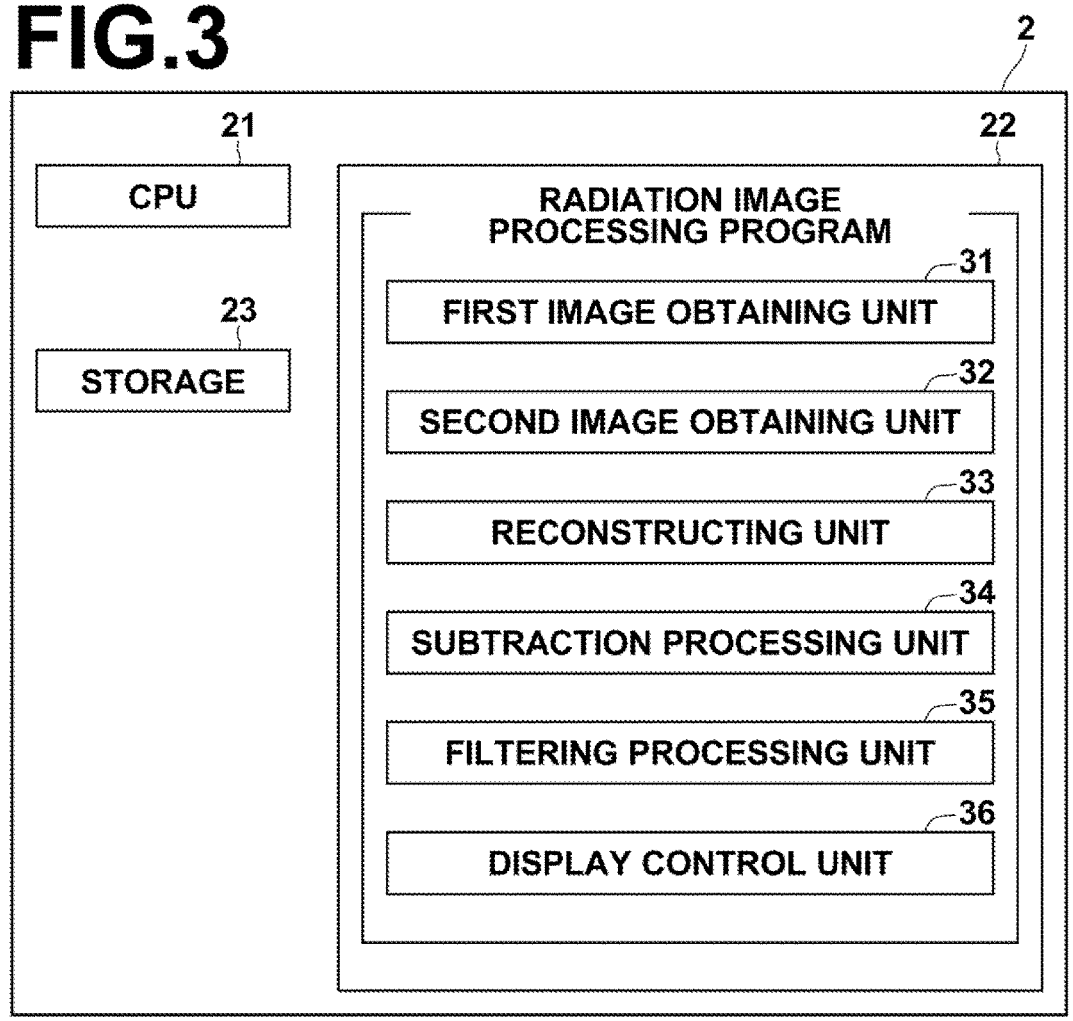

| THICKNESS OF BREAST [mm] | FIRST TOMOSYNTHESIS IMAGING | | SECOND TOMOSYNTHESIS IMAGING | |
|---|---|---|---|---|
| | T/F | TUBE VOLTAGE [kV] | T/F | TUBE VOLTAGE [kV] |
| 0-20 | W/Rh | 26 | W/Al | 26 |
| 20-30 | W/Rh | 27 | W/Al | 28 |
| 30-40 | W/Rh | 28 | W/Al | 30 |
| 40-50 | W/Rh | 29 | W/Al | 32 |
| 50-60 | W/Rh | 30 | W/Al | 34 |
| 60-70 | W/Rh | 31 | W/Al | 36 |
| 70-80 | W/Rh | 32 | W/Al | 38 |
| 80- | W/Rh | 33 | W/Al | 40 |

| 250 | 250 | 250 |
|---|---|---|
| 250 | 1000 | 250 |
| 250 | 250 | 250 |

| 1/4 | 1/4 | 1/4 |
|---|---|---|
| 1/4 | 1000 | 1/4 |
| 1/4 | 1/4 | 1/4 |

TGj-2

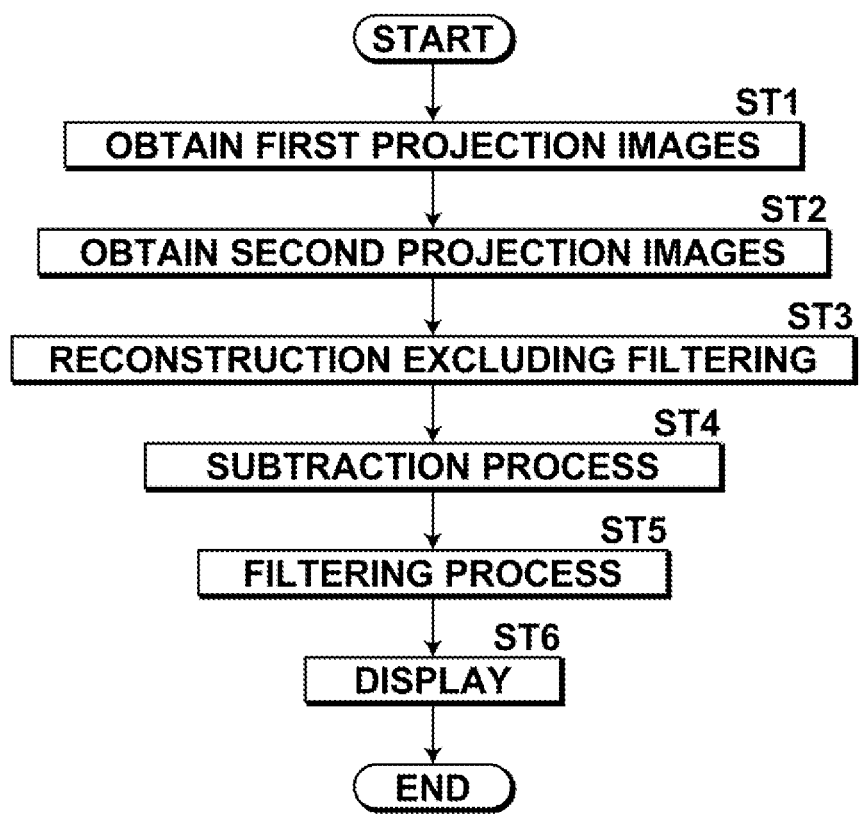

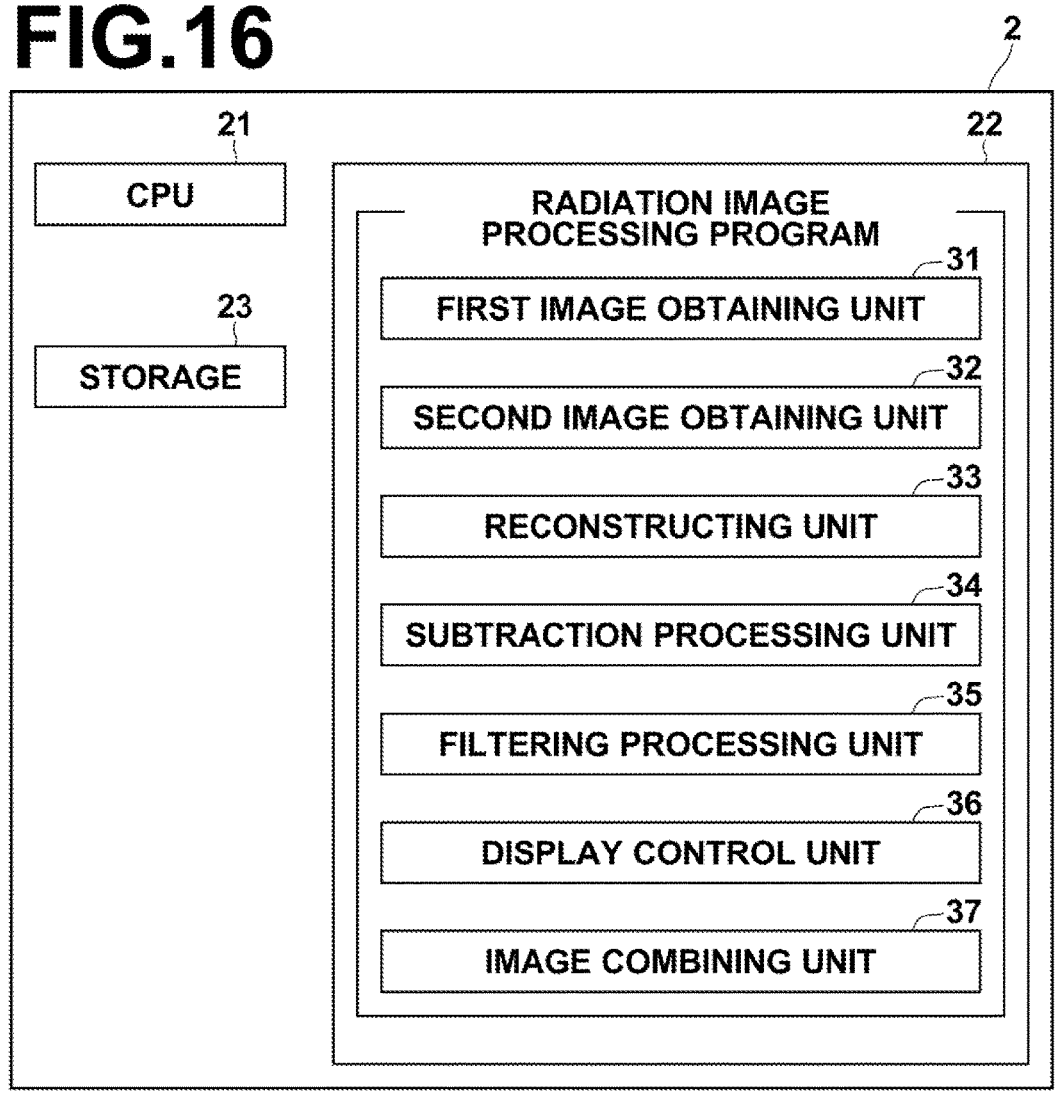

RADIATION IMAGE PROCESSING APPARATUS, RADIATION IMAGE PROCESSING METHOD, AND RECORDING MEDIUM HAVING RADIATION IMAGE PROCESSING PROGRAM STORED THEREIN

CROSS REFERENCE TO RELATED APPLICATIONS

The present application claims priority under 35 U.S.C. § 119 to Japanese Patent Application No. 2016-026615 filed on Feb. 16, 2016. The above application is hereby expressly incorporated by reference, in its entirety, into the present application.

BACKGROUND

The present disclosure is related to a radiation image processing apparatus, a radiation image processing method, and a radiation image processing program that generates subtraction images from tomographic images obtained by tomosynthesis imaging under different imaging conditions.

Recently, tomosynthesis imaging has been proposed for radiation image obtaining apparatuses that employ radiation such as X rays and gamma rays. Tomosynthesis imaging obtains images by irradiating radiation onto a subject from a plurality of radiation source positions by moving a radiation source, and generates a tomographic image in which a desired cross sectional plane is emphasized, from a plurality of projection images obtained by the imaging operations, in order to observe an afflicted portion in greater detail. In tomosynthesis imaging, the radiation source may be moved parallel to a radiation detector or moved along a circular or elliptical trajectory according to the characteristics of an imaging apparatus or necessary tomographic images. The subject is imaged at a plurality of radiation source images to obtain a plurality of projection images. A tomographic image is generated by reconstructing the projection images by an reconstruction method such as the shift and add method, the simple back projection method or the FBP method (Filtered Back Projection method).

Here, the FBP method is a reconstruction method that designates plane parallel cross sectional scanning of tomosynthesis imaging as a portion of a cone beam CT scan, and expands the filtered back projection method. If a projection image is merely back projected, noise will occur in the periphery of a coordinate position which is a target of processing. Therefore, the FBP method back projects a projection image after applying a filter thereon, to reduce blurring in images that flows in the direction of movement of the radiation source, and obtains an image closer to the intended target.

Meanwhile, there is a problem in tomosynthesis imaging that reconstructed tomographic images become blurred due to the influence of mechanical errors of an imaging apparatus, body movement of a subject caused by temporal differences among imaging operations at each of a plurality of radiation source positions, etc. If a tomographic image is blurred, it will become difficult for lesions such as fine calcifications, which are effective in early diagnosis of breast cancer, to be detected, in the case that the subject is a breast. For this reason, simple imaging is also performed when performing tomosynthesis imaging, to obtain both tomographic images, and two dimensional images. For example, radiation imaging apparatuses for imaging breasts (called mammography apparatuses) that perform both tomosynthesis imaging and simple imaging with breasts maintained in a compressed state have been proposed (refer to PCT Japanese Publication No. 2014-507250 and Japanese Unexamined Patent Publication No. 2012-166026).

In addition, subtraction processes are performed in mammography, in order to facilitate discrimination of lesions. Here, subtraction processes refer to a process in which an image corresponding to a difference in a plurality of radiation images imaged under different imaging conditions is obtained. Specifically, a subtraction process is administered for each corresponding pixel within the plurality of images, to emphasize or extract a specific portion of the subject within the radiation images, that is, to obtain a subtraction image.

There are basically two types of subtraction processes which are performed in mammography. One type of subtraction process is temporal subtraction. In temporal subtraction, an image, in which blood vessels of a breast are not emphasized, is subtracted from an image, in which the blood vessels of the breast are emphasized by imaging after injecting a contrast agent into the breast from a vein, to extract the blood vessel portions. The other type of subtraction process is energy subtraction. Energy subtraction utilizes the fact that contrast agents have different radiation absorption rates with respect to radiation having different energies. In energy subtraction, radiation having different energies are irradiated onto a breast after a contrast agent is injected, to obtain radiation images having different energies. The plurality of radiation images are weighted appropriately and differences among the radiation images are calculated, to extract the blood vessel portions of the breast. In addition, there are cases in which radiation is irradiated onto a breast at temporal intervals after a contrast agent is injected to obtain a plurality of radiation images. In such cases, the plurality of radiation images are weighted appropriately and differences among the radiation images are calculated, to ascertain the spread of the contrast agent through the blood vessel portions of the breast.

In many cases, breast cancer progresses by the blood vessel walls being weak and newly formed blood vessels that spread randomly toward the periphery increasing. The increased newly formed blood vessels increase transmissivity and are serpentine, different from normal blood vessels. Accordingly, the increased newly formed blood vessels can be extracted by employing subtraction images, thereby facilitating detection of breast cancer.

For this reason, a technique in which two radiation images to be subjected to a subtraction process are obtained to generate a subtraction image in addition to obtaining tomographic images by tomosynthesis imaging, and the subtraction image and the tomographic images are displayed has been proposed (refer to PCT Japanese Publication No. 2014-507250). In addition, a CE-DBT (Contrast Enhanced Digital Breast Tomosynthesis) technique that obtains radiation images to be subjected to subtraction processes at each radiation source position when performing tomosynthesis imaging has also been proposed (refer to Japanese Unexamined Patent Publication No. 2012-166026). According to the technique disclosed in Japanese Unexamined Patent Publication No. 2012-166026, a plurality of radiation images are obtained by irradiating radiation having different energies onto a subject while performing tomosynthesis imaging, a plurality of tomographic images having different energies are generated from the obtained plurality of radiation images, and a subtraction process is administered onto the tomographic images, to obtain subtraction images of the tomographic images (hereinafter, referred to as "tomographic subtraction images").

SUMMARY

In the case that tomosynthesis imaging is performed by the technique disclosed in Japanese Unexamined Patent Publication No. 2012-166026, the radiation source is stopped at each radiation source position, and a plurality of projection images are obtained by irradiating a subject with radiation having different energies at the stopped positions. Subtraction processes are administered on the projection images which are obtained at each radiation source position, to obtain projection subtraction images, and a subtraction projection image is reconstructed. Thereby, a tomographic subtraction image in which lesions are extracted can be generated. However, if the radiation source is stopped and two projection images are obtained at a plurality of radiation source positions, imaging will require a long amount of time. If a long amount of time is required for imaging, body movement may occur and the spread of a contrast agent will change due to the passage of time. Therefore, there is a possibility that desired tomographic images cannot be obtained. For this reason, irradiating radiation having different energies to obtain projection images while moving the radiation source may be considered, in order to shorten the amount of time required for imaging.

However, if imaging is performed while moving the radiation source, the imaging positions will differ between projection images of different energies which are to be obtained at the same imaging position. For this reason, it is necessary to generate tomographic images of different energies from each of the projection images of different energies first, and to perform subtraction processes between the tomographic images of different energies at corresponding cross sectional planes.

In the processes performed in the FBP method, which is employed to reconstruct tomographic images, back projection is performed after filtering is administered on projection images, in order to prevent the generation of blurring in images that flows in the direction of movement of the radiation source. However, if filtering is administered on the projection images, components which are not included in the original projection images will be added thereto. These components cannot be completely removed even if back projection is performed, and will appear as artifacts in the tomographic images. In addition, such artifacts appear due to the filtering process, and therefore cannot be removed by subtraction processes. For this reason, if subtraction processes are administered employing tomographic images that include such artifacts, there is a possibility that unnecessary components which are not present within subjects will appear in tomographic subtraction images as artifacts.

The present disclosure has been developed in view of the foregoing circumstances. The present disclosure enables obtainment of tomographic subtraction images having high image quality.

A radiation image processing apparatus of the present disclosure comprises:

a first image obtaining means configured to obtain a plurality of first projection images corresponding to each of a first plurality of radiation source positions by moving a radiation source relative to a detecting means and irradiating a subject with radiation from the first plurality of radiation source positions under first imaging conditions;

a second image obtaining means configured to obtain a plurality of second projection images corresponding to each of a second plurality of radiation source positions by movement of the radiation source and irradiating the subject with radiation from the second plurality of radiation source positions under second imaging conditions;

a reconstructing means configured to generate a plurality of first tomographic images and a plurality of second tomographic images for each of a plurality of cross sectional planes within the subject by reconstructing the plurality of first projection images and the plurality of second projection images employing processes excluding a filtering process in a reconstruction process that includes the filtering process;

a subtracting means configured to administer subtraction processes on the first tomographic images and the second tomographic images at corresponding cross sectional planes to generate tomographic subtraction images; and a filtering means for administering a filtering process on the tomographic subtraction images to generate processed tomographic subtraction images.

The expression "moving a radiation source relative to a detecting means" refers to a case in which only the radiation source is moved, a case in which only the detecting means is moved, and a case in which both the radiation source and the detecting means are moved.

The expression "reconstructing . . . employing processes excluding a filtering process in a reconstruction process that includes the filtering process" refers to performing reconstruction by a reconstruction process that should include a filtering process, without administering the filtering process. For example, in the aforementioned FBP method, reconstruction is performed by subjecting projection images to simple back projection after a filtering process is administered, to generate tomographic images. For this reason, in the case that the reconstruction process that should include a filtering process is a reconstruction process that employs the FBP method, reconstruction is performed only by the back projection process, without the filtering process being administered. Note that examples of methods that employ "processes excluding a filtering process" include the shift and add method, in addition to simple back projection, which is the FBP method from which the filtering process is excluded.

The expression "corresponding cross sectional planes" refers to cross sectional planes that correspond to each other in the first tomographic images and the second tomographic images, that is, the same cross sectional plane.

The "subtraction processes" may refer to temporal subtraction or energy subtraction. In the case of temporal subtraction, the first radiation image may be obtained by imaging employing a contrast agent, and the plurality of projection images may be obtained by imaging without employing the contrast agent. Conversely, the first radiation image may be obtained by imaging without employing a contrast agent, and the second images may be obtained by imaging employing the contrast agent. As a further alternative, both the first radiation image and the plurality of projection images may be obtained by imaging employing a contrast agent, in order to view the spread of the contrast agent over time.

Note that in the radiation image processing apparatus of the present disclosure, the first and second image obtaining means may obtain the plurality of first projection images and the plurality of second projection images by relatively moving the radiation source with respect to the detecting means, and repetitively irradiating radiation onto the subject according to the first imaging conditions and the second imaging conditions, alternately.

In addition, in the radiation image processing apparatus of the present disclosure, the filtering means may administer filtering processes using an emphasizing filter with respect to the direction of movement of the radiation source within the tomographic subtraction images.

The "emphasizing filter" is a filter that emphasizes pixels which are targets of filtering, by restricting the transmittance of pixels in the vicinities of the pixels which are the targets of filtering.

In addition, the radiation image processing apparatus of the present disclosure may further comprise an image combining means configured to combine processed tomographic subtraction images corresponding to each of the plurality of cross sectional planes, to generate a combined tomographic subtraction image.

In addition, in the radiation image processing apparatus of the present disclosure, the first imaging conditions and the second imaging conditions may set different energies for the radiation to be irradiated onto the subject. In this case, the tomographic subtraction images which are generated by the subtraction processes will be tomographic energy subtraction images.

In addition, the radiation image processing apparatus of the present disclosure may further comprise a display control means configured to display the processed tomographic subtraction images on a display means.

In this case, the display control means may display at least one of the plurality of first tomographic images and the plurality of second tomographic images on the display means.

In addition, the display control means may display at least one of the plurality of first tomographic images and the plurality of second tomographic images such that an abnormal portion which is specified by the processed tomographic subtraction image is emphasized.

In addition, in this case, the display control means may display the processed tomographic subtraction images overlapped with at least one of the plurality of first tomographic images and the plurality of second tomographic images.

In addition, in the radiation image processing apparatus of the present disclosure, at least one of the plurality of first tomographic images and the plurality of second tomographic images may be obtained by imaging operations that employ a contrast agent.

A radiation image processing method of the present disclosure comprises:

obtaining a plurality of first projection images corresponding to each of a first plurality of radiation source positions by moving a radiation source relative to a detecting means and irradiating a subject with radiation from the first plurality of radiation source positions under first imaging conditions;

obtaining a plurality of second projection images corresponding to each of a second plurality of radiation source positions by movement of the radiation source and irradiating the subject with radiation from the second plurality of radiation source positions under second imaging conditions;

generating a plurality of first tomographic images and a plurality of second tomographic images for each of a plurality of cross sectional planes within the subject by reconstructing the plurality of first projection images and the plurality of second projection images employing processes excluding a filtering process in a reconstruction process that includes the filtering process;

administering subtraction processes on the first tomographic images and the second tomographic images at corresponding cross sectional planes to generate tomographic subtraction images; and administering a filtering process on the tomographic subtraction images to generate processed tomographic subtraction images.

Note that the radiation image processing method of the present disclosure may be provided as a program to be executed by a computer.

According to the present disclosure, a plurality of first projection images are obtained under first imaging conditions, and a plurality of second projection images are obtained under second imaging conditions. Each of the plurality of first projection images and the plurality of second projection images are reconstructed by processes of a reconstruction method that includes a filtering process, without administering the filtering process, to obtain first tomographic images and second tomographic images. Then, subtraction processes are administered on first tomographic images and second tomographic images for corresponding cross sectional planes, to generate tomographic subtraction images.

Here, the first tomographic images and the second tomographic images are reconstructed by processes excluding a filtering process. Therefore, the tomographic subtraction images do not include components which are not originally present within the subject, that is, artifacts, which may be generated due to the filtering process. Meanwhile, blurring in images that flows in the direction of movement of the radiation source is included in the first tomographic images and the second tomographic images, because the filtering process has not been administered.

In the present disclosure, a filtering process is administered on the tomographic subtraction images, to generate processed tomographic subtraction images. Thereby, the amount of blurring that flows in the direction of movement of the radiation source is decreased. Accordingly, the present disclosure enables obtainment of tomographic subtraction images having high image quality, in which artifacts and blurring are reduced.

BRIEF DESCRIPTION OF THE DRAWINGS

FIG. 1 is a diagram that schematically illustrates the configuration of a radiation image obtaining apparatus to which a radiation image processing apparatus according to a first embodiment of the present disclosure is applied.

FIG. 2 is a diagram of the radiation image obtaining apparatus as viewed from the direction of arrow A in FIG. 1.

FIG. 3 is a diagram that schematically illustrates the configuration of the radiation image processing apparatus of the first embodiment, which is realized by installing a radiation image processing program in a computer.

FIG. 15 is a flow chart that illustrates the processes which are executed in the first embodiment.

FIG. 16 is a diagram that schematically illustrates the configuration of a radiation image processing apparatus according to a second embodiment, which is realized by installing a radiation image processing program in a computer.

DETAILED DESCRIPTION OF THE PREFERRED EMBODIMENTS

Figures 4, 5:
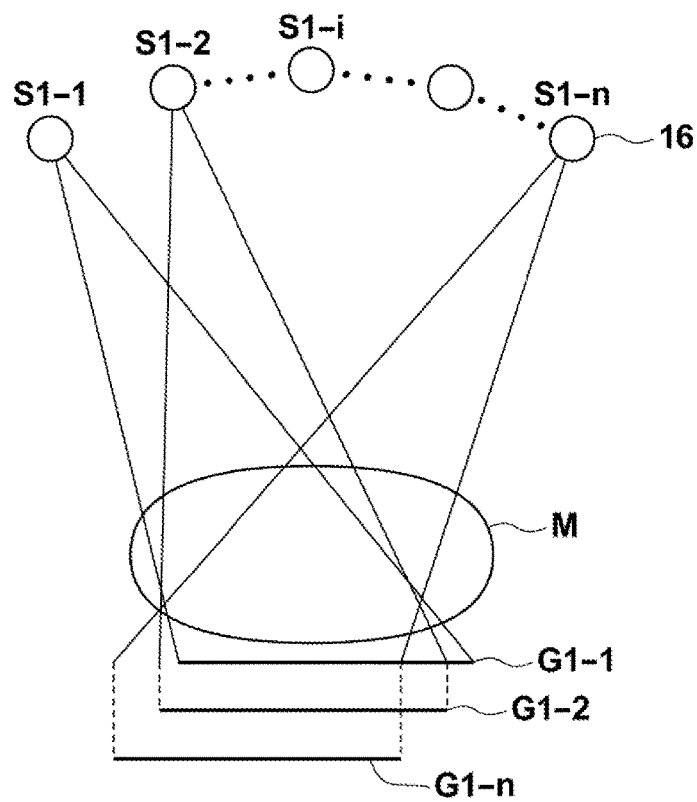
FIG. 4 is a diagram for explaining obtainment of a projection image.
FIG. 5 is a diagram that illustrates a table that lists imaging conditions.

Hereinafter, embodiments of the present disclosure will be described with reference to the drawings. FIG. 1 is a diagram that schematically illustrates the configuration of a radiation image obtaining apparatus to which a radiation image processing apparatus according to a first embodiment of the present disclosure is applied, and FIG. 2 is a diagram of the radiation image obtaining apparatus as viewed from the direction of arrow A in FIG. 1. A radiation image obtaining apparatus 1 images a breast M, which is a subject, from a plurality of radiation source positions having different imaging directions to generate a plurality of radiation images, in order to generate tomographic images by performing tomosynthesis imaging of a breast. That is, the radiation image obtaining apparatus 1 is a mammography apparatus that generates a plurality of projection images. As illustrated in FIG. 1, the radiation image obtaining apparatus 1 includes an image obtaining unit 10, a computer 2 connected to the image obtaining unit 10, a display unit 3, and an input unit 4 connected to the computer 2. The radiation image obtaining apparatus 1 according to the present embodiment also performs simple imaging as will be described later, to acquire two dimensional images, which are transmission images, of the breast M. In the present embodiment, simple imaging and tomosynthesis imaging are performed by injecting a contrast agent into the breast M.

The image obtaining unit 10 includes an arm unit 12 connected to a base (not shown) by a rotatable shaft 11. An imaging base 13 is attached to one end of the arm unit 12, and a radiation irradiating section 14 is attached to the other end of the arm unit 12 so as to face the imaging base 13. The arm unit 12 is configured so as to be able to rotate only at the end portion to which the radiation irradiating unit 14 is attached, so that it is possible to rotate only the radiation irradiation unit 14 with the imaging base 13 being fixed. Note that rotation of the arm unit 12 is controlled by the computer 2.

A radiation detector 15 such as a flat panel detector is provided within the imaging base 13. A charge amplifier for converting the charge signal read from the radiation detector 15 into a voltage signal, a correlated double sampling circuit for sampling a voltage signal output from the charge amplifier, and a circuit board provided with an A/D converter for converting the digital signal into a digital signal and the like are also provided within the imaging base 13. The radiation detector 15 corresponds to a detecting means.

The radiation detector 15 can repeatedly record and read out radiation images. It is possible to use a so called direct type radiation detector that directly receives irradiation of radiation and generates electrical charges, or a so called indirect type radiation detector which converts radiation into visible light, and then converts the visible light into electrical charge signals. In addition, as preferred methods for reading out radiation image signals, there are a so called TFT readout method in which a radiation image signal is read out by turning TFT (thin film transistor) switches ON and OFF, and a so called light readout method in which radiation image signals are read out by irradiating readout light. However, the present disclosure is not limited to these readout methods, and other methods may be employed.

An X ray source 16, which is a radiation source, is housed inside the radiation irradiation unit 14. The timings at which X rays are irradiated as radiation from the X ray source 16 and X ray generating conditions in the X ray source 16, that is, the material of the anode and the filter, as well as imaging conditions such as the tube voltage and the irradiation time, are controlled by the computer 2.

Further, a compression plate 17 disposed above the imaging base 13 to press the breast M to compress it, a support section 18 for supporting the compression plate 17, and a moving mechanism 19 for moving the support section 18 in the vertical direction of FIGS. 1 and 2, are provided on the arm unit 12. Note that the distance between the compression plate 17 and the imaging base 13, that is, the compression thickness, is input to the computer 2.

The display unit 3 is a display device such as a CRT or a liquid crystal monitor, and displays projection images, two dimensional images, tomographic images and subtraction images, which are obtained as will be described later. In addition, the display unit 3 also displays messages and the like which are necessary for operations. Note that the display unit 3 may include a built in speaker that outputs sound.

The input unit 4 comprises input devices such as a keyboard, a mouse and a touch panel, and receives operations of the radiation image obtaining apparatus 1 which are input by an operator. Also, the input unit 4 accepts various pieces of information necessary for performing tomosynthesis photographing, such as imaging conditions and commands to correct information. In the present embodiment, each part of the radiation image obtaining apparatus 1 operates according to the information input by the operator from the input unit 4.

A radiation image processing program is installed in the computer 2. In the present embodiment, the computer may be a work station or a personal computer which the operator directly operates, or may be a server computer connected to a work station or a personal via a network. The radiation image processing program is recorded and distributed on a recording medium such as a DVD (Digital Versatile Disc), CD-ROM (Compact Disc Read Only Memory), etc., and installed on the computer from the recording medium. Alternatively, the radiation image processing program is stored in a storage device or a network storage of a server computer connected to a network in an accessible state from the exterior, downloaded to a computer in response to a request, and installed.

FIG. 3 is a diagram that schematically illustrates the configuration of the radiation image processing apparatus of the first embodiment, which is realized by installing the radiation image processing program in the computer 2. As illustrated in FIG. 3, the radiation image processing apparatus includes a CPU (Central Processing Unit) 21, a memory 22, and a storage 23, as components of a standard computer configuration.

The storage 23 includes a storage device such as a hard disk or an SSD (Solid State Drive), and stores various types of data, including programs for driving each part of the radiation image obtaining apparatus 1, and the radiation image processing program. In addition, projection images acquired by tomosynthesis imaging, two dimensional images acquired by simple imaging, tomographic images, synthesized two dimensional images, and subtraction images, which are generated as will be described later, are also stored in the storage 23. Various tables to be described later are also stored in the storage 23.

The memory 22 temporarily stores programs and the like which are stored in the storage 23 so as to cause the CPU 21 to execute various processes. The radiation image processing program defines processes to be executed by the CPU 21, which are: a first image obtaining process that acquires a plurality of first projection images corresponding to each of a first plurality of radiation source positions, by moving the X ray source 16 relative to the radiation detector 15 and irradiating X rays onto the breast M at each of the plurality of radiation source positions under first imaging conditions; a second image obtaining process that acquires a plurality of second projection images corresponding to each of a second plurality of radiation source positions by movement of the X ray source 16 and irradiating X rays onto the breast M at each of the plurality of radiation source positions under second imaging conditions; a reconstructing process that generates a plurality of first tomographic images and a plurality of second tomographic images for each of a plurality of cross sectional planes within the breast M by reconstructing the plurality of first projection images and the plurality of second projection images employing processes excluding a filtering process in a reconstruction process that includes the filtering process; a subtracting process that administers subtraction processes on the first tomographic images and the second tomographic images at corresponding cross sectional planes to generate tomographic subtraction images; a filtering process that administers a filtering process on the tomographic subtraction images to generate processed tomographic subtraction images, and a display control process that causes the subtraction tomographic images and the tomographic images to be displayed by the display unit 3.

By the CPU 21 executing these processes according to the radiation image processing program, the computer 2 functions as a first image obtaining unit 31, a second image obtaining unit 32, a reconstructing unit 33, a subtraction processing unit 34, and a display control unit 36. Note that the computer 2 may include processors that respectively perform each of a first imaging process, a second imaging process, a reconstruction process, a subtraction process, a filtering process, and a display control process.

The first image obtaining unit 31 moves the X ray source 16 by rotating the arm unit 12 around the rotatable shaft 11, X rays are irradiated onto the breast M as a subject according to the first imaging conditions at a first plurality of radiation source positions due to the movement of the X ray source, the X rays transmitted through the breast M are detected by the radiation detector 15, and a plurality of first projection images G1-$i$ (i=1 to n, n is the number of radiation source positions) are obtained. FIG. 4 is a diagram for explaining obtainment of the projection images G1-$i$. As illustrated in FIG. 4, the X ray source 16 is moved to each radiation source position S1-1, 1-S2, . . . , S1-$n$, and the X ray source 16 is driven at each radiation source position to irradiate the breast M with X rays. By detecting the X rays transmitted through the breast M with the radiation detector 15, the projection images G1-1, G1-2, . . . , G1-$n$ are acquired corresponding to the respective radiation source positions S1-1 to S1-$n$. The plurality of obtained first projection images G1-$i$ are stored in the storage 23. Note that a plurality of first projection images G1-$i$ may be obtained by a program separate from the radiation image processing program and stored in the storage 23. In this case, the first image obtaining unit 31 reads out the plurality of first projection images G1-$i$ stored in the storage 23 from the storage 23 for the reconstruction process. In addition, tomosynthesis imaging operations for obtaining the plurality of first projection images G1-I will be referred to as "first tomosynthesis imaging operations".

The second image obtaining unit 32 moves the X ray source 16 by rotating the arm unit 12 around the rotatable shaft 11, X rays are irradiated onto the breast M as a subject according to the first imaging conditions at a second plurality of radiation source positions due to the movement of the X ray source, the X rays transmitted through the breast M are detected by the radiation detector 15, and a plurality of second projection images G2-$i$ (i=1 to n, n is the number of radiation source positions) are obtained. The plurality of obtained second projection images G2-$i$ are stored in the storage 23. Note that a plurality of second projection images G2-$i$ may be obtained by a program separate from the radiation image processing program and stored in the storage 23. In this case, the first image obtaining unit 31 reads out the plurality of second projection images G2-$i$ stored in the storage 23 from the storage 23 for the reconstruction process. In addition, tomosynthesis imaging operations for obtaining the plurality of second projection images G2-$i$ will be referred to as "second tomosynthesis imaging operations".

Here, in the present embodiment, the first and second tomosynthesis operations are performed by repetitively irradiating X rays onto the breast M under the first imaging conditions and the second imaging conditions alternately, while moving the X ray source 16. Thereby, the first and second image obtaining units 31 and 32 alternately obtain the first and second projection images G1-$i$, G2-$i$ as projection images G1-1, G2-1, G1-2, G2-2, . . . . In this case, the first and second projection images G1-$i$ and G2-$i$ that correspond to each other will be obtained at different radiation source positions. Note that the first and second tomosynthesis operations may be performed at first and second radiation source positons which are the same. In this case, the X ray source 16 may be ceased at each radiation source position, and the first and second tomosynthesis operations may be performed at each radiation source position. In this case, the first and second projection images G1-$i$ and G2-$i$ that correspond to each other will be obtained at the same radiation source positions.

Next, the first and second imaging conditions will be described. The X ray source 16 includes a filament for outputting an electron beam, a target for generating X rays by the electron beam colliding therewith, and a filter for adjusting the energy spectrum of X rays. The target has a plurality of different anode materials, for example Mo, Rh and W, which are provided to be selectable. The filter has a plurality of different substances, for example Mo, Rh, W and Al, which are provided to be selectable.

Imaging conditions are conditions for obtaining an appropriate radiation image by adjusting the energy spectrum (radiation quality) of X rays to be irradiated onto the breast M. For example, the imaging conditions include the type of target constituting the X ray source 16, the type of filter, X ray generating conditions including a tube voltage applied between the filament and the target, and grid conditions that indicate the presence or absence of the grid 20. It should be noted that an mAs value (tube current x radiation irradiation time) may be included as an imaging condition.

In the present embodiment, a table of the first and second imaging conditions for the first and second tomosynthesis imaging operations is stored in the storage 23. FIG. 5 is a diagram that illustrates the table of imaging conditions. As illustrated in FIG. 5, the table LUT 1 for imaging conditions prescribes first and second tomosynthesis imaging conditions corresponding to a plurality of breast thicknesses. Specifically, T/F, which indicates the type of the target and the filter, and the tube voltage, are set as the first and second imaging conditions. By referring to the table LUT 1, when the thickness of the breast is 45 mm, for example, W/Rh (target is W, filter is Rh) is set as T/F and 29 kV is set as the tube voltage in the first imaging conditions under which the first tomosynthesis imaging operations are performed. In addition, W/Al (target is W, filter is Al) is set as T/F and 32 kV is set as the tube voltage in the second imaging conditions under which the second tomosynthesis imaging operations are performed. Note that the tube voltage is higher during the second tomosynthesis imaging operations than during the first tomosynthesis imaging operations. Therefore, the breast M is irradiated with higher energy X rays during the second tomosynthesis imaging operations than during the first tomosynthesis imaging operations. Hereafter, the first tomosynthesis imaging operations will be described as being performed with low energy X rays, and the second tomosynthesis imaging operations will be described as being performed with high energy X rays. The first and second imaging conditions which are set are stored in the storage 23.

The reconstructing unit 33 generates first tomographic images and second tomographic images in which a desired cross sectional plane within the breast M is emphasized, by reconstructing the plurality of first projection images G1-$i$ and the plurality of second projection images G2-$i$ employing processes excluding a filtering process in a reconstruction process that includes the filtering process. Note that the reconstruction processes which are administered on the first projection images G1-$i$ and the second projection images G2-$i$ are the same, and therefore here, only the reconstruction process which is administered on the first projection images G1-$i$ will be described.

Figure 6:
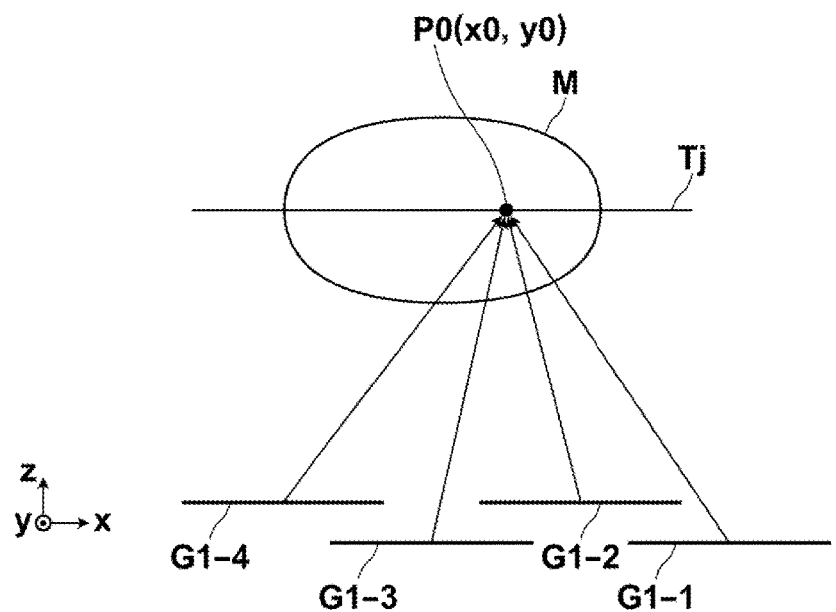
FIG. 6 is a diagram for explaining the back projection method.

The reconstructing unit 33 employs a known back projection method, such as the simple back projection method to reconstruct the first projection images G1-$i$, to generate first tomographic images TG1-$j$ for each of a plurality of cross sectional planes Tj. FIG. 6 is a diagram for explaining the back projection method. Note that here, back projection employing four first projection images, G1-1, G1-2, G1-3, and G1-4 will be described. In addition, in FIG. 6, the horizontal direction of the drawing sheet is designated as the x axis, the vertical direction of the drawing sheet is designated as the y axis, and the direction perpendicular to the drawing sheet is designated as the z axis. As illustrated in FIG. 6, the pixel values of corresponding coordinate positions within the projection images G1-1, G1-2, G1-3, and G1-4 are back projected onto a coordinate position P0 (x0, y0) on a cross sectional plane Tj within the breast M. Thereby, the pixel value of the tomographic image for a cross sectional plane z0 at the coordinate position P0 (x0, y0) is calculated, to reconstruct a first tomographic image TG1-$j$.

Figure 7:
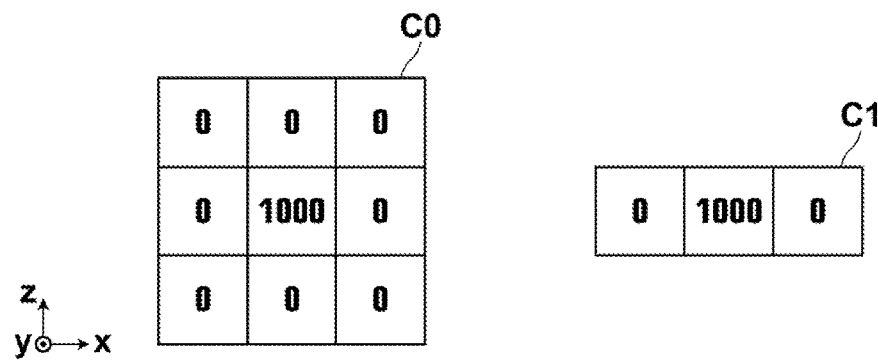
FIG. 7 is a diagram for explaining calculation of pixel values employing the back projection method.

FIG. 7 is a diagram for explaining calculation of pixel values on a cross sectional plane employing the back projection method. Note that in order to simplify the explanation here, back projection within a 3×3 range (hereinafter, referred to as "target range") on the x-z range having the coordinate position within the breast M which is to be the target of calculation (hereinafter, referred to as "target coordinate position") will be described. For the sake of explanation, if the target range is represented as an image, the target coordinate position within the breast M has a pixel value of 1000, and the pixel values of the eight coordinate positions about the periphery of the target coordinate position on the x-z plane are 0, as illustrated in C0 of FIG. 7. In this case, three coordinate positions which are arrayed in the x direction having the target coordinate position at their center within the projection images G1-1, G1-2, G1-3, and G1-4 have pixel values of (0, 1000, 0), as illustrated in F1 of FIG. 7. In addition, each of the projection images G1-1, G1-2, G1-3, and G1-4 back project pixel values onto the target coordinate position from the right, the obliquely right and downward direction, beneath, and the obliquely left and downward direction of the breast M, respectively.

Figure 8:
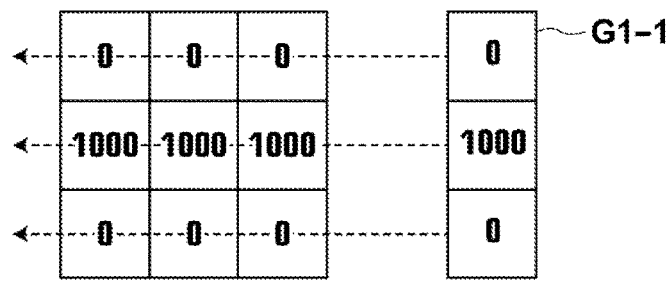
FIG. 8 is a diagram for explaining calculation of pixel values employing the back projection method.
Figure 9:
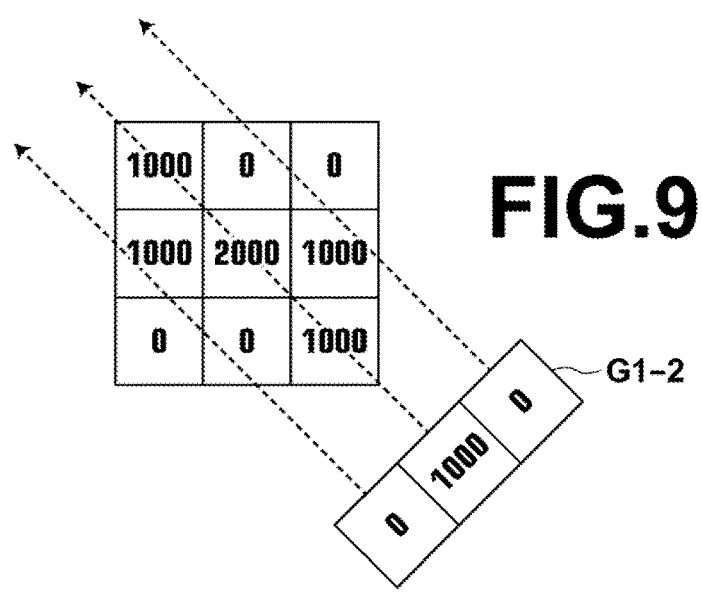
FIG. 9 is a diagram for explaining calculation of pixel values employing the back projection method.
Figure 10:
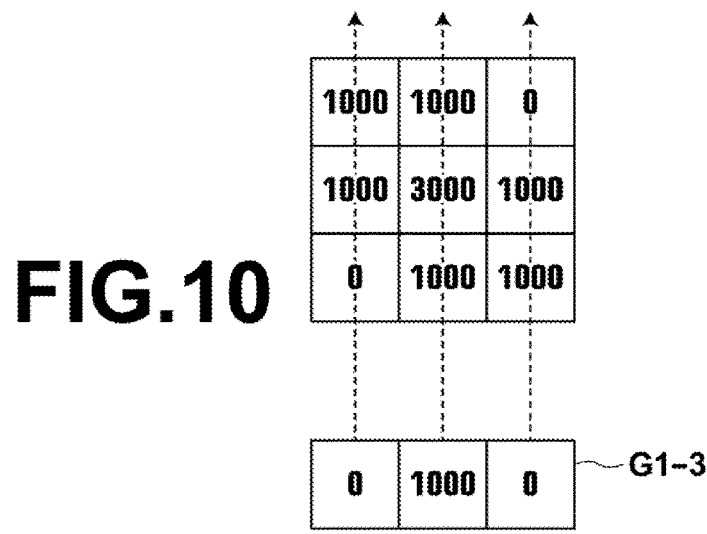
FIG. 10 is a diagram for explaining calculation of pixel values employing the back projection method.
Figure 11:
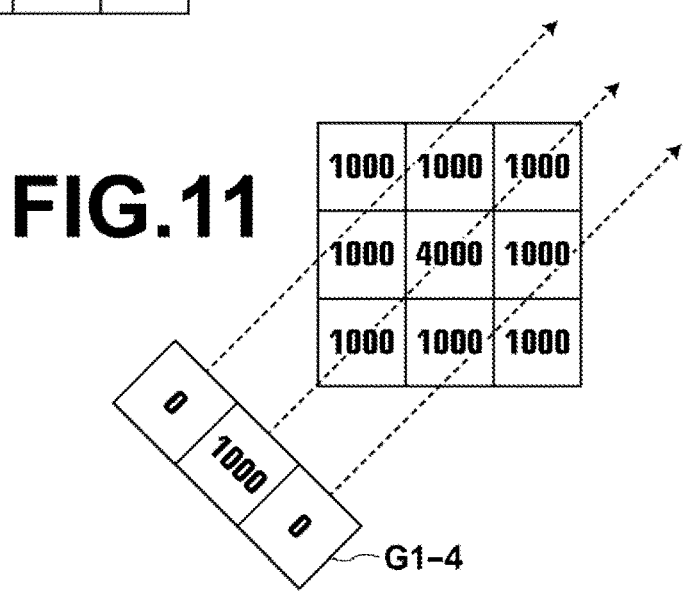
FIG. 11 is a diagram for explaining calculation of pixel values employing the back projection method.
Figures 12, 13, 14:
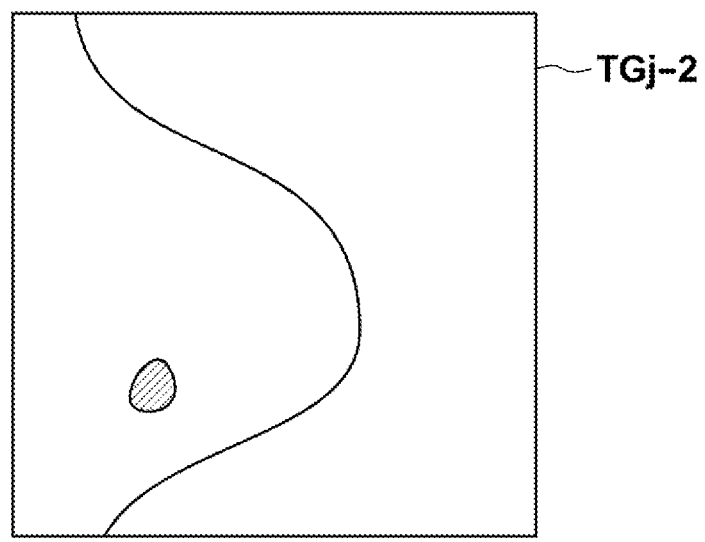
FIG. 12 is a diagram for explaining calculation of pixel values employing the back projection method.
FIG. 13 is a diagram for explaining calculation of pixel values employing the filtered back projection method.
FIG. 14 is a diagram that illustrates a state in which a second tomographic image is displayed with a portion that corresponds to an abnormal portion having color added thereto.

First, the pixel value of the target coordinate position is unknown prior to back projection. If the projection image G1-1 is back projected thereon from the right side, the upper and lower rows of the target range will become zero, and one of the left end, the center, and the right end of the middle row will become 1000. Therefore, a pixel value of 1000 is temporarily placed at these positions. FIG. 8 is a diagram that illustrates this state. Next, if the projection image G1-2 is back projected thereon from the obliquely right and downward direction in a similar manner, the pixel value of one of the lower left coordinate position, the center of the target range, and the upper right coordinate position will be 1000. Therefore, these pixel values of 1000 are added to the pixel values illustrated in FIG. 8, and the pixel values of the target range become those illustrated in FIG. 9. Further, if the projection image G1-3 is back projected from directly underneath, the pixel values of the target range become those illustrated in FIG. 10. Finally, if the projection image G1-4 is back projected from the obliquely left and downward direction, the pixel values of the target range become those illustrated in FIG. 11. In the case that the four projection images G1-1, G1-2, G1-3, and G1-4 are employed to perform back projection in this manner, the pixel values of each coordinate position within the target range are divided by four. Thereby, the pixel value of the target coordinate position will become 1000, and the pixel values of the coordinate positions in the periphery thereof will all be 250, as illustrated in FIG. 12. For this reason, blurring will be included in a tomographic image in the case that the simple back projection method is employed.

In order to reduce the amount of blurring that flows in the direction of movement of the radiation source, the conventional FBP method performs back projection after administering filtering processes on projection images that emphasize the values corresponding to the target coordinate position. For example, a one dimensional emphasizing filter that emphasizes pixel values (0, 1000, 0) such that they become (−333, 1000, −333) is employed to filter the projection images G1-1, G1-2, G1-3, and G1-4 with respect to the direction of movement of the X ray source 16, and then the filtered projection images are back projected. Thereby, the pixel values of the target range can be calculated such that the value of the target coordinate position approximates the actual value.

However, if the projection images are filtered, components which are not included in the original projection images will be added to the projection images. These components cannot be completely removed even if back projection is performed, and remain in tomographic images as artifacts. For example, if the projection images G1-1, G1-2, G1-3, and G1-4 are filtered employing the aforementioned filter that emphasizes the values corresponding to the target coordinate position to (−333, 1000, −333), and then the filtered projection images are back projected, the coordinate positions about the periphery of the target coordinate position will have pixel values of ¼, which are not actually present within the breast M. Such pixel values will appear in tomographic images as artifacts. In addition, such artifacts appear due to the filtering process, and therefore cannot be removed by subtraction processes. For this reason, if subtraction processes are administered employing tomographic images that include such artifacts, there is a possibility that unnecessary components which are not present within subjects will appear in tomographic subtraction images as artifacts.

The reconstructing unit 33 of the present embodiment generates the first tomographic images TG1-$j$ and the second tomographic images TG2-$j$ by the simple back projection method, without administering a filtering process. Note that the shift and add method may be employed instead of the simple back projection method.

The subtraction processing unit 34 generates a tomographic subtraction images TGsubj in which abnormal portions of the breast M are emphasized by calculating weighted difference values between corresponding pixels of the first tomographic images TG1-$j$ and the second tomographic images TG2-$j$ at corresponding cross sectional planes Tj. In the present embodiment, the first and second tomosynthesis imaging operations are performed by injecting a contrast agent into the breast M. In addition, the first tomographic images TG1-$j$ are obtained by low energy X rays and the second tomographic images TG2-$j$ are acquired by high energy X rays. Therefore, by properly weighting among the pixels corresponding to each other within the first tomographic images TG1-$j$ and the second tomographic images TG2-$j$, and then computing the difference values, normal blood vessel portions in the breast M are removed. As a result, the tomographic subtraction images TGsubj are those in which newly formed blood vessels attributable to breast cancer, that is, abnormal portions, are extracted. At this time, the weighted difference value can be easily calculated by aligning the first tomographic images TG1-$j$ and the second tomographic images TG2-$j$ using feature points such as the edges of structures included in the first tomographic images TG1-$j$ and the second tomographic images TG2-$j$.

The filtering processing unit 35 administers filtering processes on the tomographic subtraction images TGsubj. Specifically, the filtering processing unit 35 employs a one dimensional emphasizing filter which is utilized in the FBP method that emphasizes the pixel values of target coordinate positions to be greater than the pixel values in the peripheries thereof, to administer filtering processes on the tomographic subtraction images TGsubj in the direction of movement of the X ray source 16, to obtain processed tomographic subtraction images TG0subj. Thereby, the pixel values of coordinate positions about the peripheries of target coordinate positions within the tomographic subtraction images TGsubj can be decreased. As a result, blurring that flows in the direction of movement of the X ray source 16 can be reduced in the processed tomographic subtraction images TG0subj.

The display control unit 36 displays the processed tomographic subtraction images TGsubj and the second tomographic images TG2-$j$ on the display unit 3. Note that in the present embodiment, the second tomographic images TG2-$j$ which are generated employing the second projection images G2-I that were obtained by high energy X ray imaging are displayed. Alternatively, the first tomographic images TG1-$j$ which are obtained by low energy X ray imaging may be displayed. At this time, the portion in a displayed tomographic image TGj that corresponds to the abnormal portion within a processed tomographic subtraction image TG0subj for a corresponding cross sectional plane may be emphasized. For example, as illustrated in FIG. 14, a color may be imparted to a portion corresponding to an abnormal portion within a second tomographic image TG2-$j$. In FIG. 14, the imparted color is indicated by hatching. In addition, the portion corresponding to the abnormal portion within the second tomographic image TG2-$j$ may be surrounded by a frame or an arrow may be provided, to emphasize the portion corresponding to the abnormal portion. Alternatively, a first tomographic image TG1-$j$ or a second tomographic image TG2-$j$ and a processed tomographic subtraction image TG0subj at a corresponding cross sectional plane may be aligned, overlapped, and displayed. As a further alternative, only a processed tomographic subtraction image TG0subj may be displayed.

Next, the processes which are performed by the first embodiment will be described. FIG. 15 is a flow chart that illustrates the processes which are performed by the first embodiment. When the input unit 4 accepts an instruction to start processing by an operator, tomosynthesis imaging operations are performed according to the first imaging conditions, and the first image obtaining unit 31 obtains a plurality of first projection images G1-$i$ (step ST1). Next, tomosynthesis imaging operations are performed according to the second imaging conditions, and the second image obtaining unit 32 acquires a plurality of second projection images G2-$i$ (step ST2). Note that the tomosynthesis imaging operations according to the second imaging conditions may be performed prior to the tomosynthesis imaging operations according to the first imaging conditions, such that the second projection image G2-$i$ are obtained first.

Then, the reconstructing unit 33 generates first tomographic images and second tomographic images in which a desired cross sectional plane within the breast M is emphasized, by reconstructing the first projection images G1-$i$ and the second projection images G2-$i$ employing processes excluding a filtering process in a reconstruction process that includes the filtering process (Reconstruction Excluding Filtering Process; step ST3). Thereafter, the subtraction processing unit 34 administers subtraction processes on the first tomographic images TG1-$j$ and the second tomographic images TG2-$j$, to generate tomographic subtraction images TGsubj (step ST4). Further, the filtering processing unit 35 administers filtering processes on the tomographic subtraction images TGsubj, to generate processed tomographic subtraction images TG0subj (step ST5). Next, the display control unit 36 displays the second tomographic images TG2-$j$ with an abnormal portion of the breast M, which is specified by the processed tomographic subtraction images TG0subj, emphasized therein on the display unit 3 (step ST6), and the process ends.

As described above, in the first embodiment, the plurality of first projection images G1-$i$ and the plurality of second projection images G2-$i$ are reconstructed by processes other than a filtering process in a reconstruction method that includes the filtering process, to obtain the first tomographic images TG1-$j$ and the second tomographic images TG2-$j$. Then, the subtraction processes are administered with respect to the first tomographic images TG1-$j$ and the second tomographic images TG2-$j$, to obtain the tomographic subtraction images TGsubj.

Here, the plurality of the first projection images G1-$i$ and the plurality of the second projection images G2-$i$ are reconstructed by processes other than a filtering process, specifically, only by the back projection process. Therefore, components that are not actually present within the breast M, which is the subject, that is, artifacts which may be generated by the filtering process, will not be included in the tomographic subtraction images TGsubj. On the other hand, the tomographic subtraction images TGsubj include blurring that flows in the direction of movement of the radiation source, because the filtering process has not been administered.

In the present embodiment, the filtering process is administered on the tomographic subtraction images TGsubj, to generate the processed tomographic subtraction images TG0subj. Thereby, the blurring that flows in the direction of movement of the radiation source included in the tomographic subtraction images TGsubj is reduced. Accordingly, the present embodiment enables obtainment of processed tomographic subtraction images TG0subj having high image quality, in which artifacts and blurring that flows in the direction of movement of the radiation source are reduced.

Next, a second embodiment of the present disclosure will be described. FIG. 16 is a diagram that schematically illustrates the configuration of a radiation image processing apparatus according to the second embodiment. Components which are the same as those illustrated in FIG. 3 are denoted by the same reference numerals in FIG. 16, and detailed descriptions thereof will be omitted. The radiation image processing apparatus according to the second embodiment differs from the first embodiment in that it further comprises an image combining unit 37 that combines the processed tomographic subtraction images TG0subj to generate a combined tomographic subtraction image.

The image combining unit 37 adds the plurality of processed tomographic subtraction images TG0subj, which are generated for each of the plurality of cross sectional planes Tj, at corresponding pixel positions, to generate the combined tomographic subtraction image. The combined tomographic subtraction image which is generated in this manner virtually represents a transmission image of the breast M and is equivalent to a subtraction image which is obtained by standard X ray imaging.

Note that the image combining unit 37 may add the plurality of first tomographic images TG1-$j$, the plurality of second tomographic images TG2-$j$, the plurality of first projection images G1-$i$, or the plurality of second projection images G2-$i$ at corresponding pixel positions, to generate a combined first tomographic image, a combined second tomographic image, a combined first projection image, or a combined second projection image.

In addition, the image combining unit 37 may generate a maximum value projection image by the MIP method that extracts the maximum values at corresponding pixel positions within images as the combined image, instead of adding the plurality processed tomographic subtraction images, the plurality of first tomographic images, the plurality of second tomographic images, or the plurality of projection images. Alternatively, a minimum value projection image which is obtained by the minIP method that extracts the minimum values at corresponding pixel positions within images may be generated as the combined image.

In each of the embodiments described above, the breast M is injected with the contrast agent is subjected, and then the first and second tomographic imaging operations are performed. Alternatively, only one of the first tomographic imaging operations of the breast M injected with the contrast agent and the second tomosynthesis imaging operations of the breast M injected with the contrast agent may be performed. For example, the first tomographic imaging operations may be performed for the breast M prior to injection of the contrast agent, and the second tomographic imaging operations may be performed for the breast M following injection of the contrast agent. In this case, the processed tomographic subtraction images TG0subj will not be energy subtraction images, but will be a temporal subtraction images. In addition, in the case that the first and second tomosynthesis imaging operations are performed for the breast M following injection of the contrast agent, a temporal difference will exist between the first tomosynthesis imaging operations and the second tomosynthesis imaging operations. Therefore, the spread of the contrast agent can be observed based on the obtained processed tomographic subtraction images TG0subj.

In the embodiments described above, the subject is the breast M, but the subject is not limited to being a breast. It goes without saying that any arbitrary part of the human body, such as the chest and the abdomen, may be the subject.

Hereinafter, the operational effects of the present embodiment will be described.

Radiation is alternately irradiated onto the breast M under the first imaging conditions and the second imaging conditions alternately, while moving the X ray source relative to the detecting means, to obtain the plurality of first projection images and the plurality of second projection images. Thereby, imaging operations for obtaining the plurality of first projection images and the plurality of second projection images can be performed at high speed.

The filtering process employing the emphasizing filter is administered onto the tomographic subtraction images in the direction of movement of the radiation source. Thereby, blurring that flows in the direction of movement of the radiation source within the tomographic subtraction images can be positively decreased.

The abnormal portion which is specified by the processed tomographic subtraction image is emphasized when displaying at least one of the plurality of first tomographic images and the plurality of second tomographic images. Thereby, the abnormal portions within the first and second tomographic images can be accurately discriminated.

The processed tomographic subtraction image and at least one of the plurality of first tomographic images and the plurality of second tomographic images are overlapped when displaying at least one of the plurality of first tomographic images and the plurality of second tomographic images. Thereby, Thereby, the abnormal portions within the first and second tomographic images can be accurately discriminated.

What is claimed is:
1. A radiation image processing apparatus comprising:
a first image obtaining unit configured to obtain a plurality of first projection images corresponding to each of a first plurality of radiation source positions by moving a radiation source relative to a detecting unit and irradiating a subject with radiation from the first plurality of radiation source positions under first imaging conditions;

a second image obtaining unit configured to obtain a plurality of second projection images corresponding to each of a second plurality of radiation source positions by movement of the radiation source and irradiating the subject with radiation from the second plurality of radiation source positions under second imaging conditions;

a reconstructing unit configured to generate a plurality of first tomographic images and a plurality of second tomographic images for each of a plurality of cross sectional planes within the subject by reconstructing the plurality of first projection images and the plurality of second projection images employing processes excluding a filtering process in a reconstruction process that includes the filtering process;

a subtracting unit configured to administer subtraction processes on the first tomographic images and the second tomographic images at corresponding cross sectional planes to generate tomographic subtraction images; and a filtering unit configured to administer a filtering process on the tomographic subtraction images to generate processed tomographic subtraction images.

2. A radiation image processing apparatus as defined in claim 1, wherein
the first and second image obtaining units obtain the plurality of first projection images and the plurality of second projection images by relatively moving the radiation source with respect to the detecting unit, and repetitively irradiating radiation onto the subject according to the first imaging conditions and the second imaging conditions, alternately.

3. A radiation image processing apparatus as defined in claim 1, wherein
the filtering unit is further configured to administer filtering processes using an emphasizing filter with respect to a direction of movement of the radiation source within the tomographic subtraction images.

4. A radiation image processing apparatus as defined in claim 1, further comprising:
an image combining unit configured to combine processed tomographic subtraction images corresponding to each of the plurality of cross sectional planes, to generate a combined tomographic subtraction image.

5. A radiation image processing apparatus as defined in claim 1, wherein
the first imaging conditions and the second imaging conditions set different energies for the radiation to be irradiated onto the subject.

6. A radiation image processing apparatus as defined in claim 1, further comprising:
a display control unit configured to display the processed tomographic subtraction images on a display unit.

7. A radiation image processing apparatus as defined in claim 6, wherein
the display control unit is further configured to display at least one of the plurality of first tomographic images and the plurality of second tomographic images on the display unit.

8. A radiation image processing apparatus as defined in claim 7, wherein
the display control unit is further configured to display at least one of the plurality of first tomographic images and the plurality of second tomographic images such that an abnormal portion which is specified by the processed tomographic subtraction image is emphasized.

9. A radiation image processing apparatus as defined in claim 7, wherein
the display control unit is further configured to display the processed tomographic subtraction images overlapped with at least one of the plurality of first tomographic images and the plurality of second tomographic images.

10. A radiation image processing apparatus as defined in claim 1, wherein
at least one of the plurality of first tomographic images and the plurality of second tomographic images is obtained by imaging operations that employ a contrast agent.

11. A radiation image processing method, comprising:
obtaining a plurality of first projection images corresponding to each of a first plurality of radiation source positions by moving a radiation source relative to a detecting unit and irradiating a subject with radiation from the first plurality of radiation source positions under first imaging conditions;

obtaining a plurality of second projection images corresponding to each of a second plurality of radiation source positions by movement of the radiation source and irradiating the subject with radiation from the second plurality of radiation source positions under second imaging conditions;

generating a plurality of first tomographic images and a plurality of second tomographic images for each of a plurality of cross sectional planes within the subject by reconstructing the plurality of first projection images and the plurality of second projection images employing processes excluding a filtering process in a reconstruction process that includes the filtering process;

administering subtraction processes on the first tomographic images and the second tomographic images at corresponding cross sectional planes to generate tomographic subtraction images; and administering a filtering process on the tomographic subtraction images to generate processed tomographic subtraction images.

12. A non-transitory recording medium having a radiation image processing program stored therein, the radiation imaging processing program causing a computer to execute procedures of:
obtaining a plurality of first projection images corresponding to each of a first plurality of radiation source positions by moving a radiation source relative to a detecting unit and irradiating a subject with radiation from the first plurality of radiation source positions under first imaging conditions;

obtaining a plurality of second projection images corresponding to each of a second plurality of radiation source positions by movement of the radiation source and irradiating the subject with radiation from the second plurality of radiation source positions under second imaging conditions;

generating a plurality of first tomographic images and a plurality of second tomographic images for each of a plurality of cross sectional planes within the subject by reconstructing the plurality of first projection images and the plurality of second projection images employing processes excluding a filtering process in a reconstruction process that includes the filtering process;

administering subtraction processes on the first tomographic images and the second tomographic images at corresponding cross sectional planes to generate tomographic subtraction images; and administering a filtering process on the tomographic subtraction images to generate processed tomographic subtraction images.

13. The radiation image processing apparatus according to claim 1, further comprising:

a display controller configured to control a display to display the processed tomographic subtraction images.

* * * * *